United States Patent [19]
Merry et al.

[11] Patent Number: 5,935,152
[45] Date of Patent: Aug. 10, 1999

[54] PORTABLE DEFIBRILLATOR HAVING RETRACTABLE HOOKS

[75] Inventors: Rodney J. Merry, Woodinville; Thomas K. Mehrkens, Bellevue; Shawn R. Bertagnole, Seattle; John C. Daynes, Redmond, all of Wash.

[73] Assignee: Physio-Control Manufacturing Corporation, Redmond, Wash.

[21] Appl. No.: 08/984,389

[22] Filed: Dec. 3, 1997

[51] Int. Cl.[6] .................................................. A61N 1/375
[52] U.S. Cl. .................................................................. 607/5
[58] Field of Search ......................... 607/5, 36; D24/167; D8/367, 373

[56] References Cited

U.S. PATENT DOCUMENTS

D. 320,653  10/1991  Jones et al. .

OTHER PUBLICATIONS

Protocol Systems, Inc., sales brochure for Propaq 100 Series monitors available for sale prior to Dec. 3, 1997.

*Primary Examiner*—Scott M. Getzow
*Attorney, Agent, or Firm*—Christensen O'Connor Johnson & Kindness PLLC

[57] ABSTRACT

A portable defibrillator having a defibrillator circuit, a body for housing a defibrillator circuit, and a hook coupled to the body is disclosed. The hook is positionable in an extended position and a retracted position. When in the extended position, the hook is poised to receive a member of an external structure, such as a gurney or hospital bed, and thereby enables the defibrillator to hang from the external structure. The body of the defibrillator may provide a deflectable member positioned to engage a depression formed in the outer surface of the hook when the hook is in the extended position, thus retaining the hook in the extending position. In a similar fashion, the deflectable member may be used to retain the hook in the retracted position. A user interface panel may be disposed on the front of the body of the defibrillator for providing information to and receiving information from a user of the defibrillator. The user interface panel is oriented on the front of the body to face at an upward angle relative to the base. Furthermore, electrical connection sites for coupling external electronic instruments to the defibrillator may also be provided. The electrical connection sites are recessed back from the front of the defibrillator and are further disposed on a panel extending outward from a side of the defibrillator. A method of suspending a portable defibrillator from an external structure by coupling a selectively positionable hook to the defibrillator and hanging the defibrillator from the external structure via the hook is also disclosed.

22 Claims, 8 Drawing Sheets

PORTABLE DEFIBRILLATOR HAVING RETRACTABLE HOOKS

FIELD OF THE INVENTION

The invention relates to portable external defibrillators and, more particularly, to portable defibrillators having the ability to hang from an external structure.

BACKGROUND OF THE INVENTION

A variety of circumstances can cause a human heart to lose its natural rhythm and begin to fibrillate or flutter in an irregular manner. At that point, blood is no longer pumped efficiently throughout the body. The heart can be defibrillated and returned to its normal rhythmic beating by the application of a powerful electrical current of short duration. It is crucial to defibrillate the heart quickly after the onset of fibrillation. Consequently, there is a need for portable defibrillators that can be easily transported to a victim suffering fibrillation of the heart in order to apply a defibrillating electrical current. In addition, there is a need for defibrillators designed to be conveniently and unobtrusively transported along with the patient to a health care facility.

During the period after a heart beat has been restored to normal, it is essential to continuously monitor the heart, so as to ensure that the heart does not begin to fibrillate again. Conventional defibrillators with monitoring circuitry are readily available. However, once attached to a patient, conventional defibrillators are awkward to transport thereafter in the vicinity of the patient due to the characteristics of the defibrillators' construction.

One solution to the problem of transporting a defibrillator along with a patient includes manually carrying the defibrillator alongside the patient. If the patient is being transported on a gurney, the defibrillator may be stored on a rack beneath the gurney or placed directly on the gurney above the head or below the feet of the patient. Each of these solutions, however, has significant drawbacks.

It is clearly impractical to have someone personally carry the defibrillator during the entire time the patient is being treated and transported to a health care facility. Stowing the defibrillator beneath the gurney requires that the gurney be fitted with a rack, and also renders the defibrillator relatively inaccessible so that, for example, where the defibrillator incorporates a monitor, medical personnel have difficulty monitoring the patient's physiological condition while the patient is being moved.

The most common solution to the problem, placing the defibrillator on the gurney, is far from ideal due to the limited available space on the gurney and the relative inaccessibility of the defibrillator. As noted, the defibrillator is typically placed below the feet or above the head of the patient, not near the patient's midsection where defibrillation and monitoring take place. Moreover, conventional defibrillators have a generally horizontal orientation wherein a small display screen is disposed on a front side of the defibrillator that is smaller in length and width than the top or bottom sides. When the defibrillator is set down on a gurney with the bottom side facing the gurney (i.e., front side facing horizontally), the screen is low and faces outward, not upward, making it difficult for medical personnel standing above the defibrillator to observe the monitor.

Conventional defibrillators also have electrical connection sites for coupling cables of other electronic instruments to the defibrillators. However, the electrical connection sites are flush with the front or rear of the defibrillator. Cables connected to these connection sites are subject to incidental impacts to the defibrillator that may dislodge the cables from the connection sites, resulting in the disconnection of the other electronic instruments to the defibrillator. Accordingly, there is a need for a defibrillator designed for easy and unobtrusive transport that includes electrical connection sites resistant to incidental impacts.

SUMMARY OF THE INVENTION

A portable defibrillator constructed according to the invention is conveniently attachable to an external structure, such as a gurney or hospital bed, and remains readily accessible to medical personnel using the defibrillator. The defibrillator includes a body that houses a defibrillator circuit and a hook that is coupled to the body. In accordance with the invention, the hook is positionable in an extended position and a retracted position. When in the extended position, the hook extends outward from the body of the defibrillator may then receive a member of an external structure, thereby enabling the defibrillator to hang from the external structure. In the retracted position, the hook is held close to the body of the defibrillator and is thereby prevented from the entangling with wires in the vicinity of the defibrillator, such as the electrical lead wires that connect the defibrillator electrodes with the defibrillator.

In one aspect of the invention, a hook that is coupled to a portable defibrillator includes a central body shaped with a generally bent configuration. The hook further includes a cylindrical member connected to the central body such that the cylindrical member extends transversely from the central body with respect to the curvature of the bent configuration. The cylindrical member may be separately attached or integrally formed with the central body of the hook.

In a further aspect of the invention, the body of the portable defibrillator includes a slot that receives the transverse cylindrical member of the hook. The slot may be configured so that the hook rotates about an axis defined by the cylindrical member, thereby permitting the hook to pivot from the extended position to the retracted position, or vice versa. The body of the defibrillator may further provide a deflectable member with a lip that mates with a corresponding depression formed on the hook for retaining the hook in either the extended or retracted position.

In yet a further aspect of the invention, the portable defibrillator includes a user interface panel disposed on the front of the defibrillator body. The user interface is oriented to face at an upward angle relative to the base of the defibrillator. Furthermore, the user interface panel is oriented on the front of the body to extend substantially above an obstruction, such as a patient's leg, when the defibrillator is placed behind the obstruction. Constructed in this fashion, the user interface panel of the portable defibrillator remains readily accessible when medical personnel are standing above the defibrillator or when the defibrillator is placed behind an obstruction.

A portable defibrillator constructed according to the invention may also provide electrical connection sites to which cables from other electronic instruments may connect, thereby electrically coupling other electronic instruments to the defibrillator. The electrical connection sites are recessed back from the front of the defibrillator. Furthermore, the electrical connection sites are disposed on a panel extending outward from a side of the defibrillator. Constructed in this fashion, the portable defibrillator provides electrical connection sites in a position that reduces the risk of dislodging the plugs of electrical cables attached to the connection sites due to incidental external impacts to the defibrillator.

The invention further includes a method for suspending a portable defibrillator from an external structure, such as a gurney or hospital bed. According to the method of the invention, a hook is coupled to the portable defibrillator such that the hook is positionable in an extended position or a retracted position relative to the defibrillator. The hook is positioned in the extended position and the defibrillator is brought close to the external structure from which it will hang. The defibrillator is oriented so that the hook, in the extended position, receives a member of the external structure. The defibrillator is then released, thereby allowing the defibrillator to hang from the external structure via the defibrillator's extended hook. The hook may be coupled to the portable defibrillator such that the hook rotates. In that case, the step of positioning the hook in the extended position is accomplished by rotating the hook from the retracted position to the extended position.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 1:
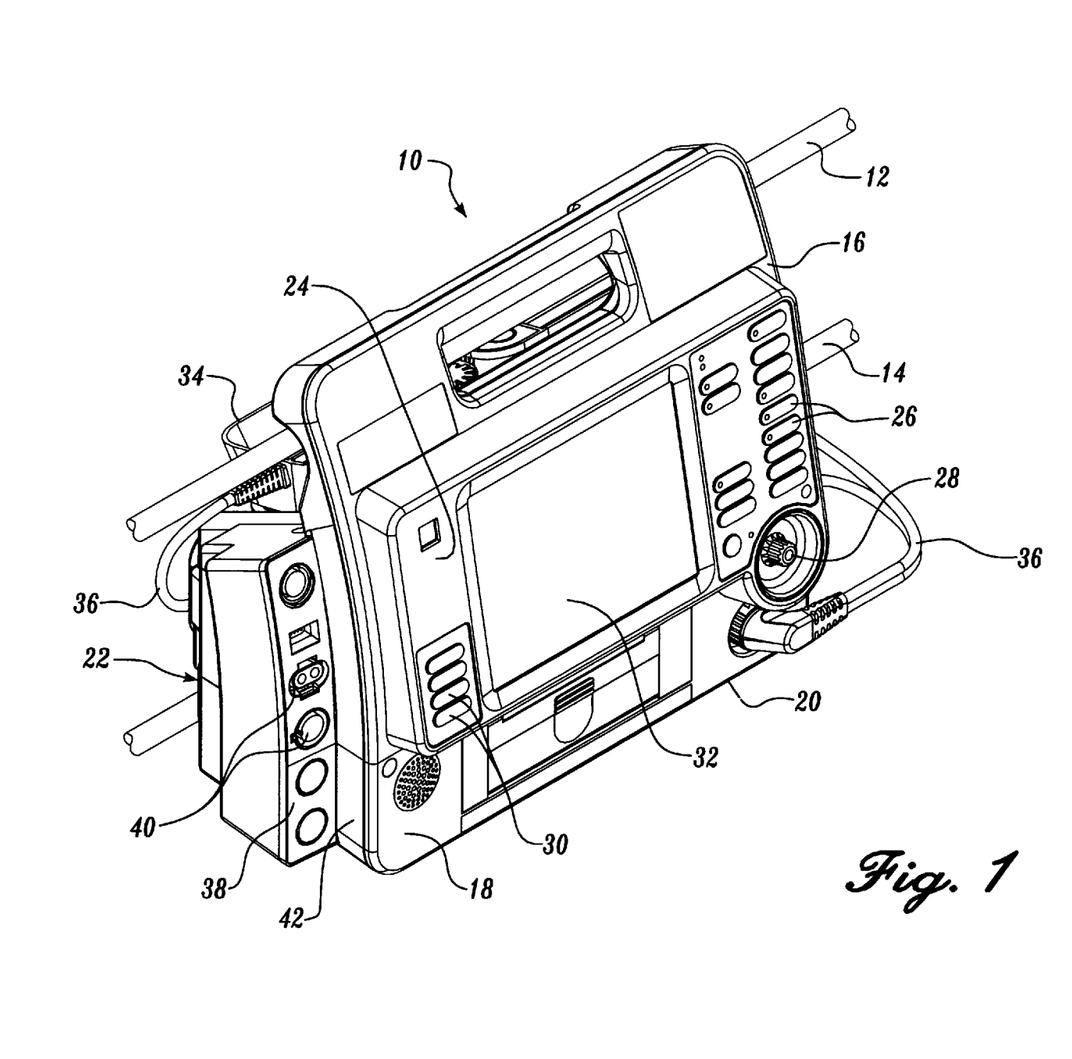
FIG. 1 is a three-dimensional front view of a defibrillator constructed in accordance with the invention and shown in an environment where it is hanging from horizontally-disposed members of an external structure.

In FIG. 1, a portable defibrillator 10, constructed in accordance with the invention, is shown hanging on support members 12 and 14 of an external structure, such as the side rails of a gurney or hospital bed. The defibrillator 10 includes defibrillator and monitor circuitry (not shown) and a body 16 for housing the defibrillator and monitor circuitry. The body has a front 18, a base 20, and a rear 22. Progressing upwards from the base 20, the front 18 is angled back toward the rear 22. In the embodiment illustrated, the front 18 curves back toward the rear 22.

Disposed on the front 18 is a user interface panel 24 for exchanging information with a user of the defibrillator. The user interface panel 24 may include a variety of buttons 26, knobs 28, keys 30, or other input means for receiving information from the user. Preferably, the user interface panel 24 also has a screen 32 for displaying information to the user. The user interface panel 24, including the screen 32, is disposed on the front 18 of the body 16 to face at an upward angle relative to the base 20 of the defibrillator. In a preferred embodiment of the invention, the defibrillator body 16 is shaped to secure the user interface panel 24 at an upward angle, thereby providing medical personnel standing above the defibrillator with an enhanced ability to view the screen and access the defibrillator controls.

The defibrillator 10 shown in FIG. 1 includes electrodes 34 and leads 36 for applying a defibrillating pulse to a patient. The leads 36 electrically couple the electrodes 34 with the defibrillator circuitry, and conduct defibrillating pulses. The defibrillator circuitry, electrodes, and leads, and the interconnections thereof, are of conventional design and are constructed by means known in the art. The leads 36 may also be used to conduct electrocardiogram or other physiological signals sensed by the electrodes to monitor circuitry in the defibrillator.

A panel 38 with a plurality of electrical connection sites 40 provides an interface for electrically connecting other medical instruments (not shown) to the defibrillator. The electrical connection sites 40 are designed and constructed to mate with corresponding plugs of other medical instruments that may be used in conjunction with the defibrillator. Appropriate electronics of conventional design are included in the defibrillator to permit the other medical instruments to interface with the defibrillator and carry out their intended function.

The panel 38 is recessed back from the front 18 of the defibrillator, thereby reducing the risk of dislodging plugs connected to the connection sites 40 due to incidental impacts to the front 18 or side 42 of the defibrillator. In addition, the panel 38, with the connection sites 40 disposed on the front thereof, extends outward from the side 42 of the defibrillator, thereby providing further protection to the plugs from impacts to the defibrillator.

Figure 2:
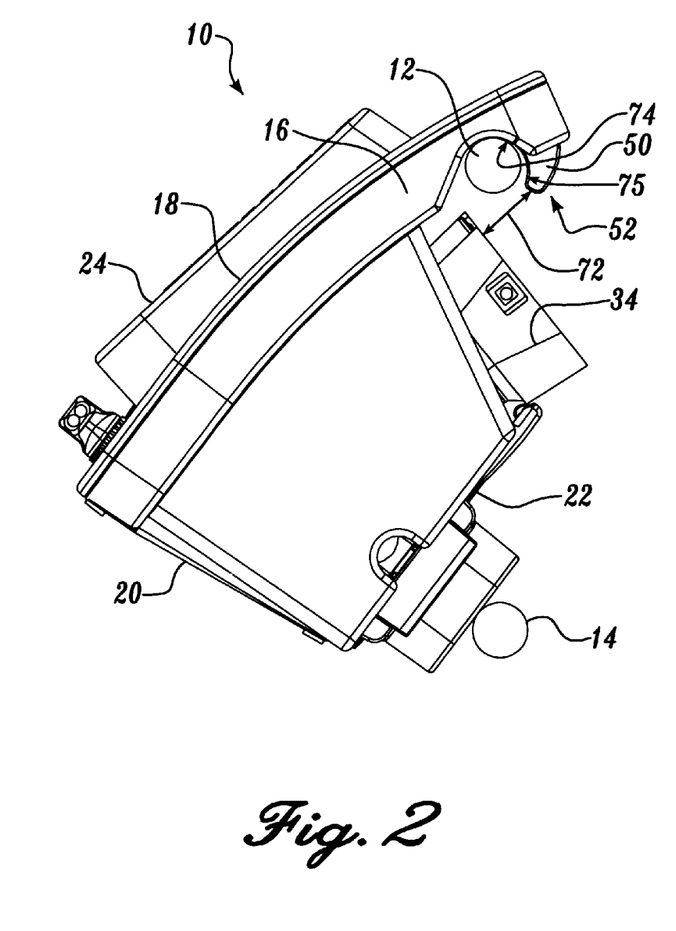
FIG. 2 is a side view of the defibrillator and environment shown in FIG. 1 with the electrical lead wires that extend between the electrodes and the defibrillator removed.

The external structural members 12, 14 shown in FIG. 1 are not part of the portable defibrillator 10, but are included in FIG. 1 to show an environment in which the defibrillator may be used. As shown in FIGS. 1 and 2, the defibrillator can hang from a member 12 and rest against another member 14. Alternatively, if the external structure does not have a member 14, the defibrillator may hang from the member 12 alone. In the environment shown in FIGS. 1 and 2, the members 12, 14 are horizontally disposed bars with one bar 12 disposed vertically above the other bar 14. The bars, in this case, may represent a section of the frame of a gurney on which a patient is transported.

To enable the defibrillator 10 to hang from an external structure, such as a gurney, the defibrillator is provided with at least one hook 50 coupled to the body 16 as shown in FIG. 2. According to the invention, the hook is positionable in an extended position or a retracted position relative to the body. In the embodiment illustrated in FIGS. 2 and 4, the hook 50 is rotatable between an extended position 52 and a retracted position 54. In the extended position 52, the hook is poised to receive a structural member 12 (e.g., a bar in a gurney frame), and transfer the weight of the defibrillator to the structure, thereby enabling the defibrillator to hang from the structure.

Figure 4:
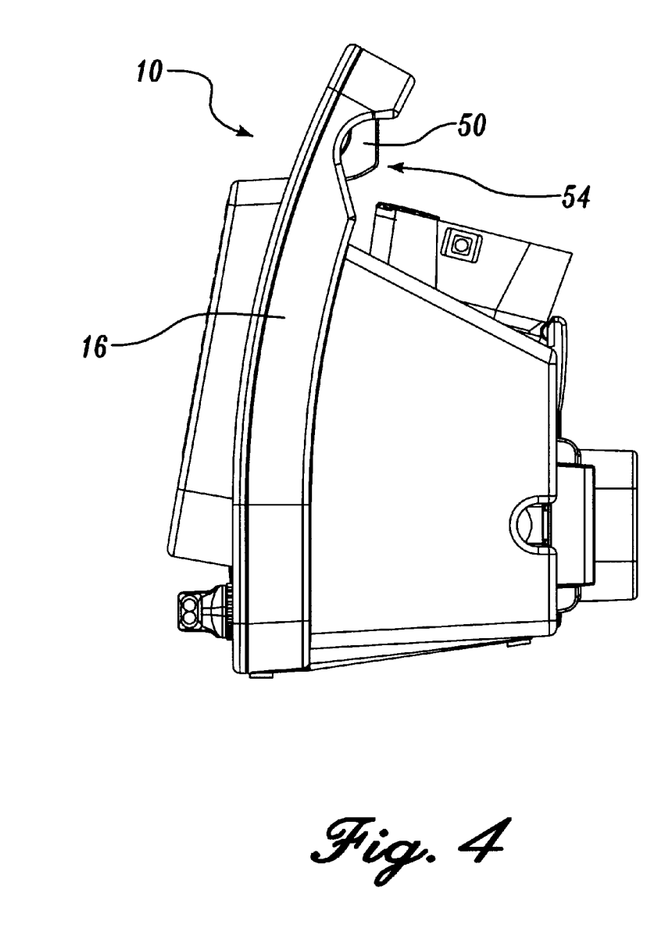
FIG. 4 is a side view of the defibrillator shown in FIG. 3, but with the hooks shown in the retracted position and the electrical lead wires that extend between the electrodes and the defibrillator removed.

The defibrillator 10 is suspended from a structure by first positioning the hook 50 in the extended position 52. The defibrillator is then lifted to a position adjacent the structure, whereby the extended hook 50 receives the structural member 12. It is appreciated that a gap 72 between the tip of the extended hook 50 and the electrodes 34 is sized sufficiently to permit passage of the structural member 12. Once the hook 50 receives the structural member 12, the defibrillator 10 is released and the structure supports the defibrillator via the defibrillator's extended hook. The gap 72 is also sized to provide clearance over the electrodes 34 for the extended hook to retract when the defibrillator is not hanging from a structure, as shown in FIG. 4.

The inside periphery 74 of the handle and the inside periphery 75 of extended hook complement the exterior shape of the structural member 12 from which the defibrillator hangs. In the illustrated embodiment, the inside peripheries 74 and 75 are curved and correspond with the cylindrical shape of the structural member 12. However, it is appreciated that the structural member 12 may have a variety of shapes and contours which the inside peripheries 74 and 75 may be shaped to match.

In many circumstances, it is advantageous to couple the hook 50 to the body 16 of the defibrillator at a position forward from the rear 22 of the defibrillator. This configuration is illustrated in FIG. 2. In FIG. 2, the defibrillator 10 is shown hanging from an external structure that includes members 12 and 14. When the defibrillator 10 hangs from structural member 12, the rear 22 of the defibrillator rests against structural member 14. Because the hook 50 is coupled to the body 16 of the defibrillator at a position forward of the rear 22, when the defibrillator 10 is hanging from structural member 12 and resting against structural member 14, the defibrillator 10 is rotated about an axis defined by the structural member 12. In essence, the structural member 14 pushes the defibrillator base 20 forward about that axis. Because the center of gravity of the defibrillator 10 is rotated away from a position vertically below the handle, the defibrillator 10 bears against the structural member 14, providing greater stability to the defibrillator. The defibrillator 10 in this position is less likely to bounce or swing away from the external structure when the structure is being moved. Furthermore, when hanging from an external structure in this manner, the defibrillator 10 positions the user interface panel 24 to face upward at a greater angle than when the defibrillator is at rest on its base 20. Medical personnel are thereby provided even more convenient access to the user interface panel 24.

Figure 3:
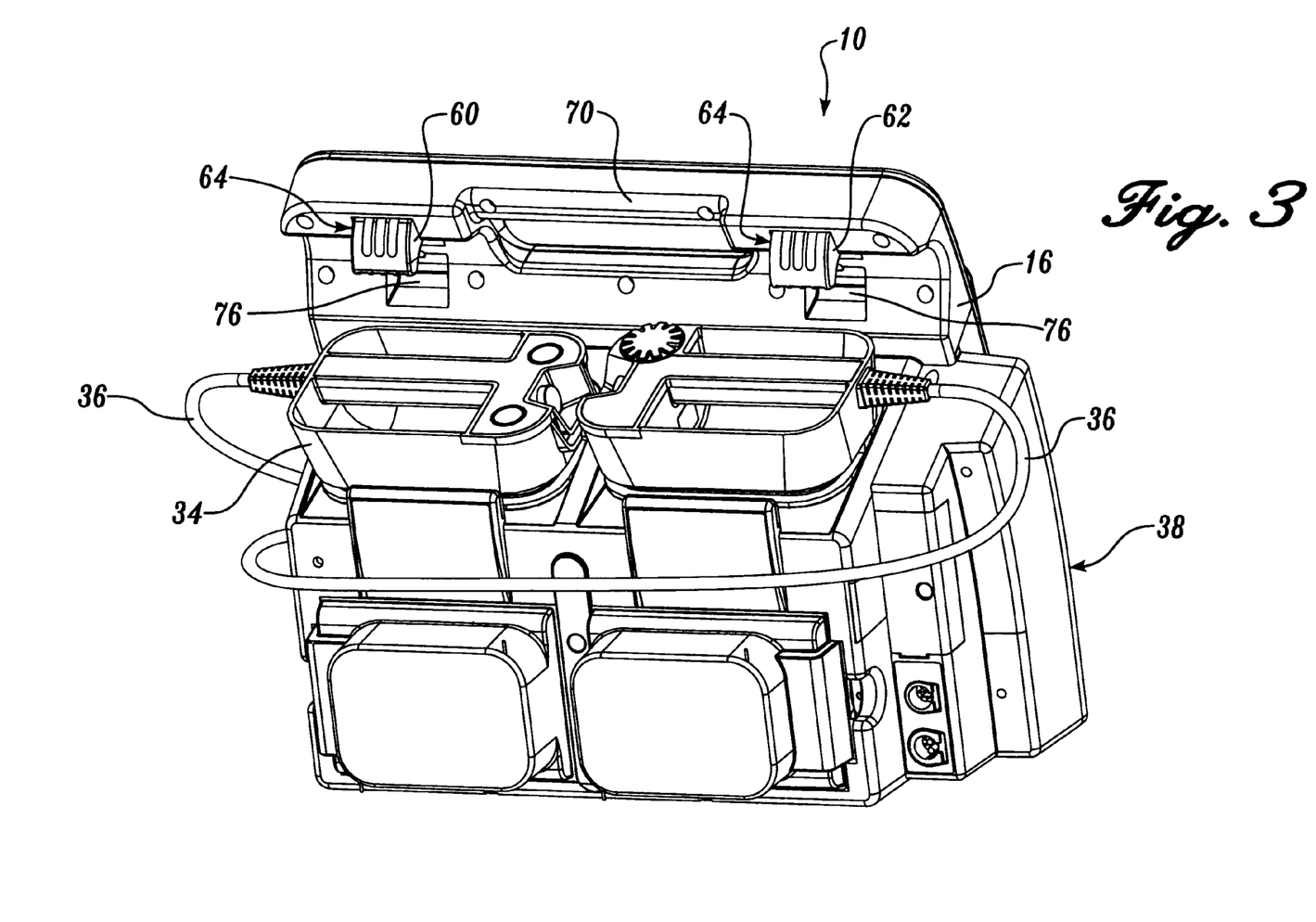
FIG. 3 is a three-dimensional rear view of a defibrillator constructed in accordance with the invention having two hooks shown in the extended position.

Referring now to FIG. 3, the defibrillator 10 is shown having two hooks 60 and 62 coupled to the body 16. The defibrillator 10 has a handle 70 that a user of the defibrillator may grasp for lifting or carrying the defibrillator. Hooks 60 and 62 are coupled to the body 16 with one hook on each side of the handle 70. The hooks 60 and 62 may be individually rotated between an extended position and a retracted position. In FIG. 3, the hooks 60 and 62 are illustrated in the extended position. Alternatively, it may be advantageous to physically interconnect the hooks 60 and 62 so that the hooks extend or retract simultaneously. While use of a single hook is encompassed within the scope of the invention, having two or more hooks provides the defibrillator 10 with greater stability when hanging from an external structure.

In the embodiment shown in FIG. 3, when hooks 60 and 62 are placed in the extended position as shown, the hooks are rotated outwardly away from the body 16. Fully extended, hooks 60 and 62 are capable of receiving a member 12 of an external structure. However, when the hooks 60 and 62 are extended and the defibrillator is not hanging on an external structure, the electrode leads 36 or wires of other nearby electronic devices (not shown) may become entangled in the hooks. As a solution to this problem, the invention provides a retracted position for the hooks, as shown in FIG. 4. When the hooks 60 and 62 are retracted to the retracted position, the hooks are rotated inwardly towards the body 16 and are received within recesses 76 (see FIGS. 3 and 9) defined in the body. The recesses 76 are sized to receive the retracted hook and thereby prevent the hook from entangling the electrode leads 36 or other wires.

Figures 5, 6:
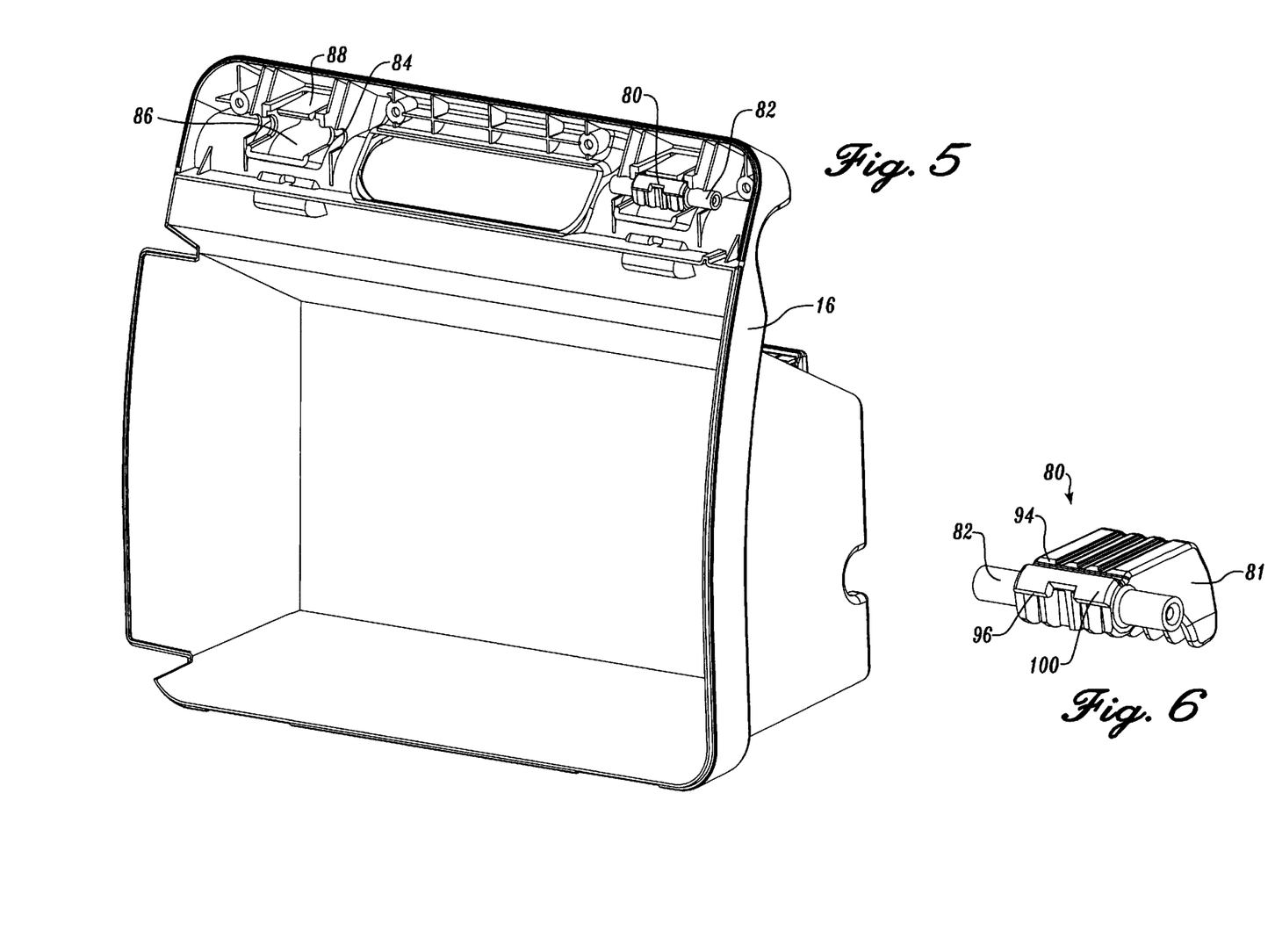
FIG. 5 is a three-dimensional front view of the interior of the rear section of the defibrillator body with one hook installed.
FIG. 6 is a three-dimensional view of a hook constructed in accordance with the invention.

Referring now to FIG. 6, a hook 80 constructed in accordance with the principles of the invention is shown. The hook 80 is formed of a central body with a cylindrical pivot member 82 transversely disposed with respect to the curvature of the hook. The hook 80 may be formed of plastic or any other suitable material.

FIG. 5 illustrates the manner in which the hook 80 may be coupled to the body 16 of the defibrillator. In FIG. 5, the details of the interior of the defibrillator handle portion are shown. However, it should be understood that the details of the remaining, lower portion of the defibrillator body have been removed to simplify the illustration. The details of the lower portion are not necessary to understand the manner in which the hook 80 is coupled to the body 16.

Referring to FIG. 5, a slot 84 defined in the body 16 of the defibrillator is sized for receiving the cylindrical pivot member 82. The hook 80 is coupled to the body 16 by first passing the hook 80 through an aperture 86 bounded on opposite sides by the slot 84. The outer ends of the cylindrical pivot member 82 are secured within the slot 84. The hook 80 is then able to pivot about the longitudinal axis of the cylindrical pivot member 82 and rotate between an extended position and a retracted position, as shown in FIGS. 2 and 4. It is appreciated that alternative means of coupling a hook to the body are available, such as inserting the outer ends of a transverse hook member (e.g., cylindrical member 82) into slotted tracks that bound opposite sides of the aperture 86, thereby permitting the hook to slide away from and towards the body to arrive at extended and retracted positions, respectively. Likewise, conventional hinge mechanisms may be used.

Figure 7:
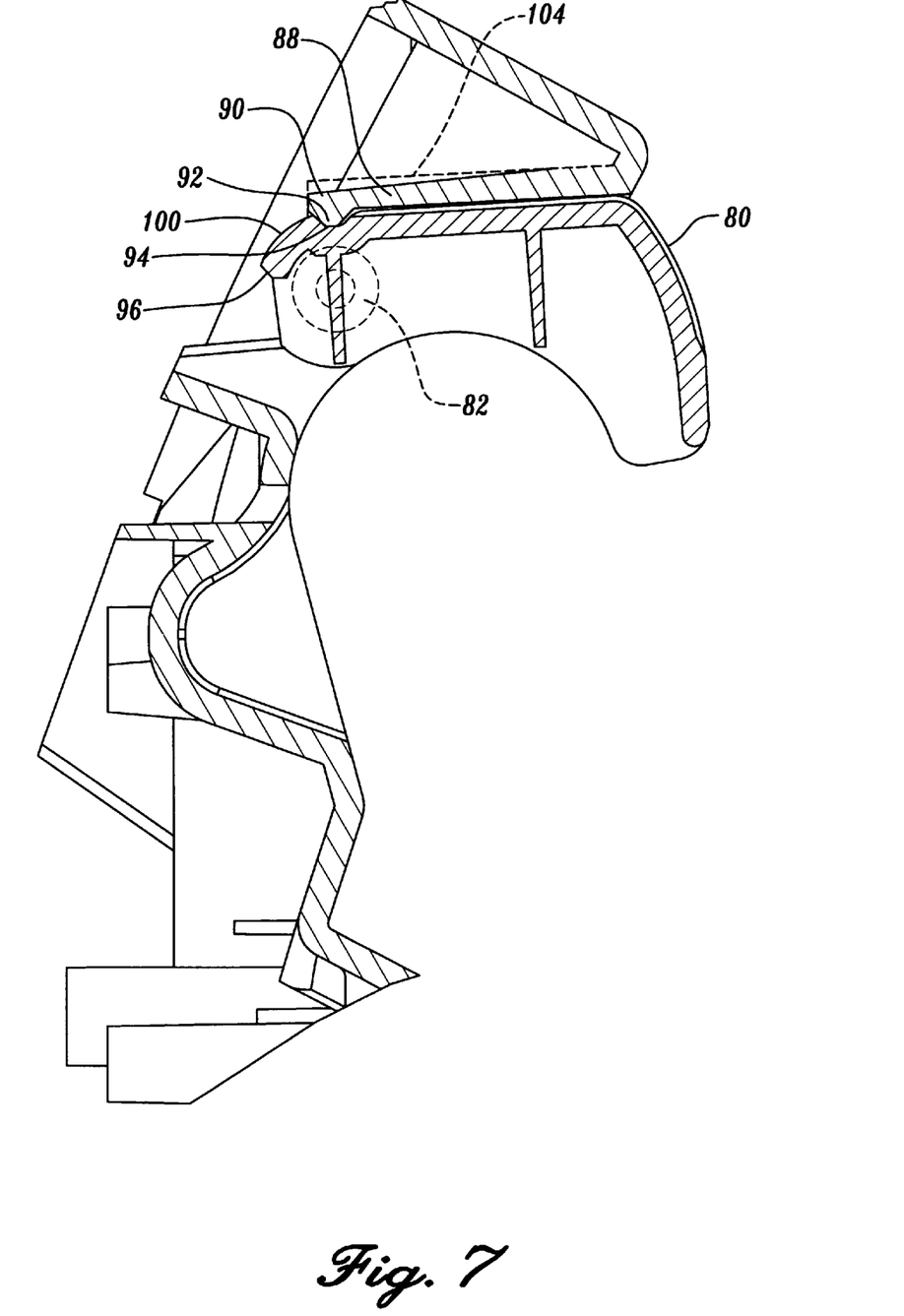
FIG. 7 is a cross-section side view of a hook installed in the defibrillator body with the hook in the extended position.
Figure 8:
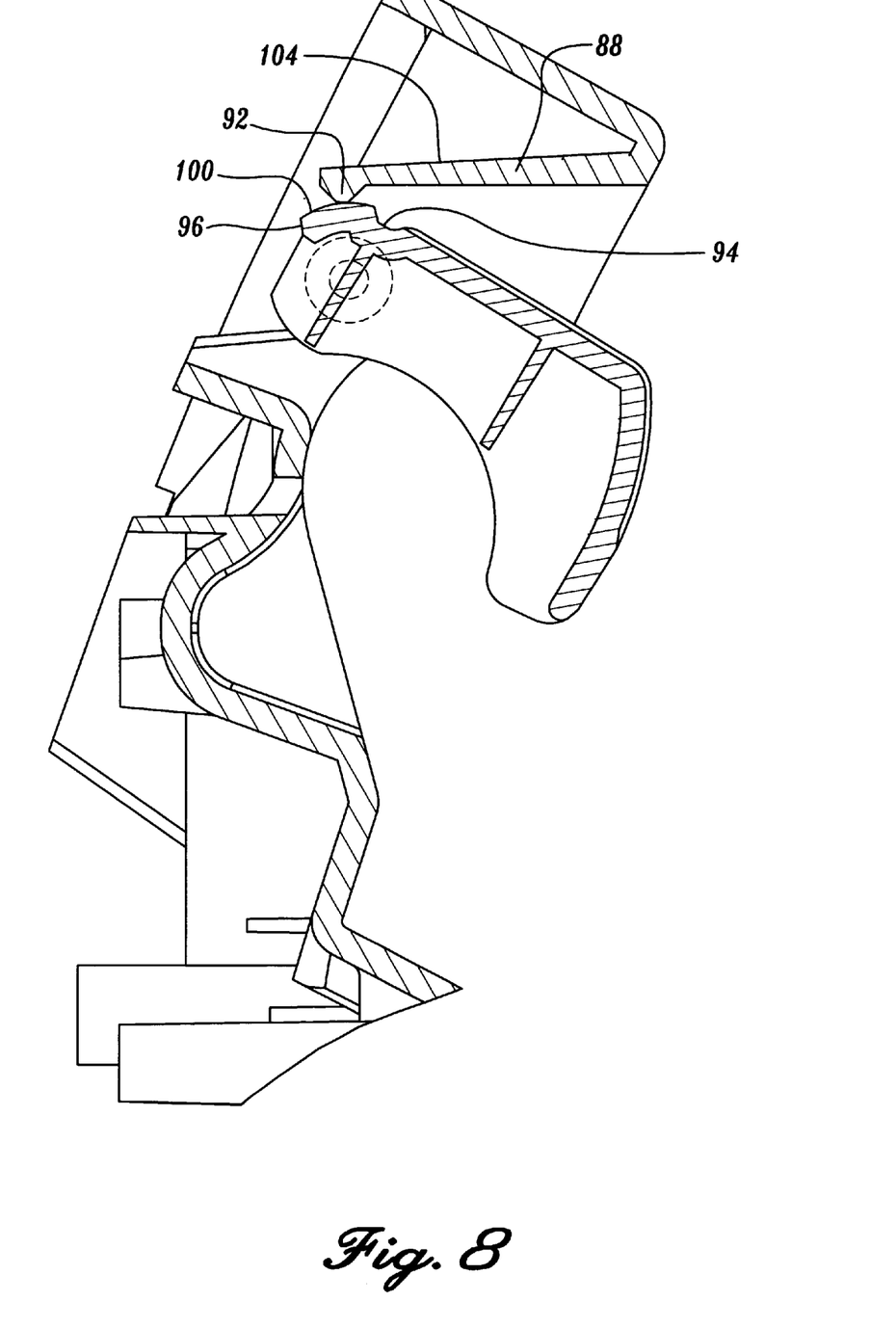
FIG. 8 is a cross-section side view of a hook installed in the defibrillator body with the hook in an intermediate position between the extended and retracted positions.
Figure 9:
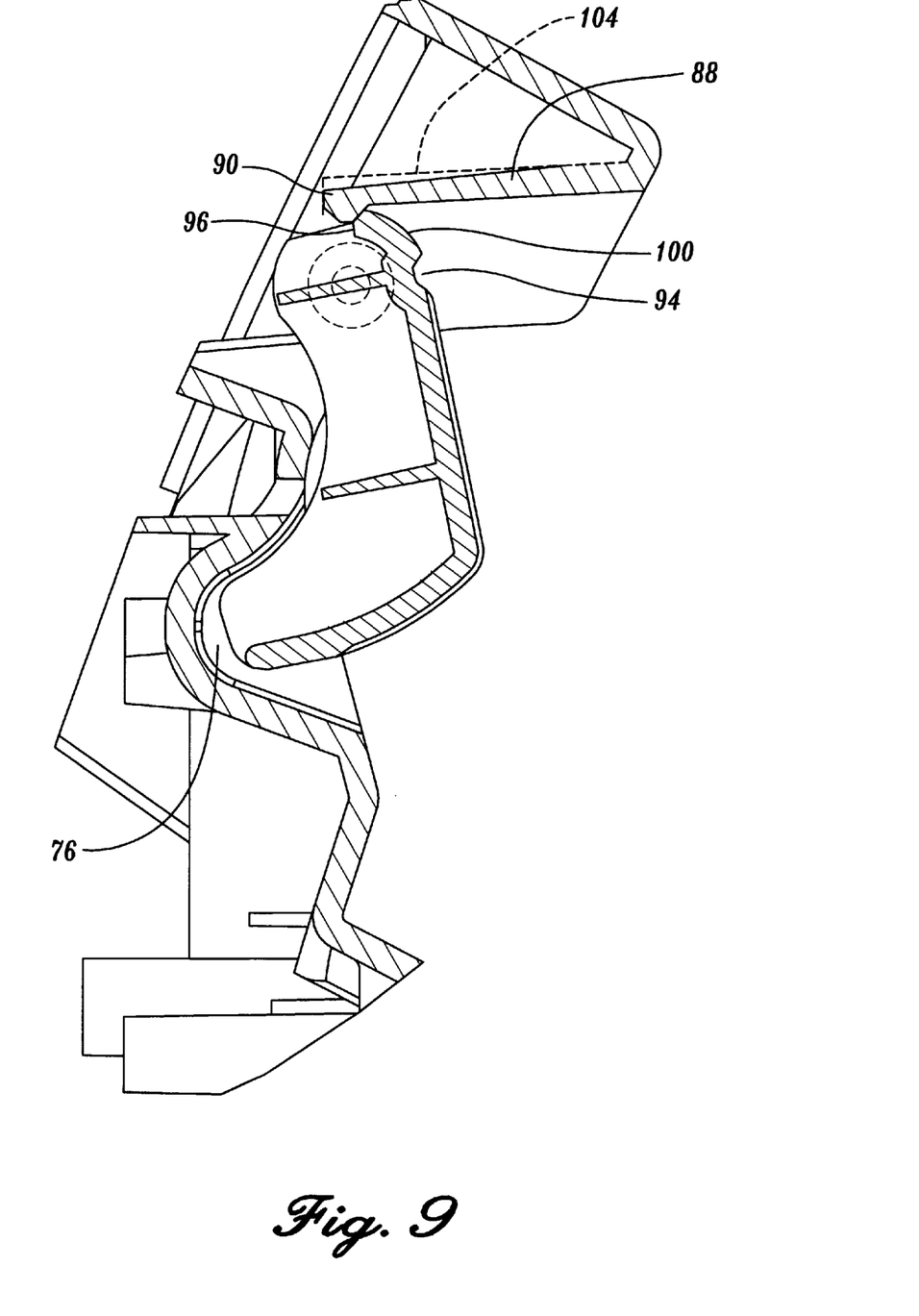
FIG. 9 is a cross-section side view of a hook installed in the defibrillator body with the hook in the retracted position.

The defibrillator 10 further includes a deflectable member 88 projecting from the body 16 into the aperture 86 for retaining the coupled hook 80 in an extended or retracted position. As depicted in FIGS. 7–9, an edge 90 of the deflectable member 88 physically contacts the hook 80 when the hook is installed. The edge 90 has a protrusion 92 projecting toward the surface of the hook 80. The hook has a corresponding depression 94 for receiving the protrusion 92 when the hook 80 is in the extended position. Preferably, the deflectable member 88 is biased towards the hook, thus causing the protrusion 92 to positively engage the depression 94 and retain the hook in the extended position. In this manner, an additional force is needed to counteract the bias force for disengaging the protrusion 92 from the depression 94 when rotating the hook from the extended to the retracted position.

While the protrusion 92 and the corresponding depression 94 may be of any suitable shape for engaging and retaining the hook in the extended position, in the embodiment shown, the protrusion 92 is a lip extending along the edge 90 of the deflectable member 88, and the depression 94 is a groove defined in the surface of the hook 80 to mate with the protrusion 92. Specifically, in FIG. 6, groove 94 is defined adjacent to the cylindrical pivot member 82 and is oriented parallel to the longitudinal axis of the cylindrical pivot member. The groove 94 is positioned on the hook 80 to engage the protrusion 92 of the deflectable member 88 when the hook is rotated to the extended position (FIG. 7).

Spaced apart from the groove 94 is an interior edge 96 of the hook surface. The interior edge 96 is similarly defined adjacent to the cylindrical pivot member 82 and parallel to the longitudinal axis of the cylindrical pivot member.

Between the interior edge 96 and the groove 94, the surface of the hook 80 defines a ridge 100. As the hook 80 is rotated (FIG. 8) from the extended position to the retracted position (FIG. 9), the protrusion 92 of the deflectable member 88 disengages the groove 94, passes over the ridge 100, and ultimately engages the interior edge 96 of the hook surface. The reverse of this process is used to disengage the hook from the retracted position and rotate the hook to the extended position. When the protrusion 92 of the deflectable member 88 passes over the ridge 100 on the hook 80, the protrusion 92 forces the deflectable member 88 to flex away from the hook to the position 104 shown in FIG. 8 and by dotted line in FIGS. 7 and 9. The deflectable member 88 reacts with a biasing force opposite the flexing motion, thus retaining the protrusion 92 on the surface of the hook 80 at all times.

The deflectable member 88 is preferably constructed of a firm but flexible material such as plastic. However, those of ordinary skill in the art will appreciate that various other materials could be used to form the deflectable member 88 such as resins, metals, etc.

As another aspect of the present invention, the defibrillator 10 includes a user interface panel 24. The user interface panel 24 shown in FIG. 10 is positioned on the front 18 of the defibrillator at a height such that if the defibrillator is placed between the legs of a patient or behind some other type of low-lying obstruction, the display screen 32 and the user interface panel 24 remain disposed substantially above the legs or obstruction and accessible to the medical personnel using the defibrillator. As the positioning of the user interface panel 24 is largely dependent on the shape of the defibrillator housing to which it is secured, placement of the user interface panel at a height to extend above a patient's legs or other obstruction can be achieved by shaping the defibrillator housing to secure the user interface panel at the selected height.

In one embodiment of the invention, the front 18 of the defibrillator is approximately 13 inches high (measured from the handle 70 to the base 20) and 14 inches wide (measured between the sides 42). Beginning at 4 inches from the base 20, the user interface panel extends upward about 10 inches (bottom to top). From the front 18 to the rear 22, the defibrillator has a depth measuring approximately 8 inches. Accordingly, it should be appreciated that the front 18 has a height and width (13 inches by 14 inches) defining an area that is greater than the area defined by the width and depth (14 inches by 8 inches) of the base 20. The foregoing measurements are exemplary of the principles of the invention and do not further limit the scope of the invention as defined by the appended claims. Constructed according to the principles of the invention, the defibrillator 10 is thus vertically oriented and has a user interface panel 24 that is more readily accessible to users of the defibrillator than the low-profile defibrillators of the prior art. A defibrillator constructed in accordance with the invention is valuable to the medical profession because the monitor screen and input keys are more readily viewed and accessed when the defibrillator is placed on the floor, when hanging from a side bar of a gurney, when placed next to or between an obstruction such as a patient's legs, or in any other situation in which the user of the defibrillator is looking down at the defibrillator. In all these situations, the user interface panel of the defibrillator faces upward toward the user of the defibrillator. In this manner, the defibrillator is better able to provide critical medical information and receive instruction from a user with less delay.

While the preferred embodiment of the invention has been illustrated and described, it will be appreciated that various changes can be made therein without departing from the spirit and scope of the invention. For example, the dimensions of the user interface panel 24 and the angle at which it is mounted on the defibrillator 10 may be changed to better suit the environment in which the defibrillator is used. The defibrillator 10 may also be equipped with a plurality of retractable hooks 80 if more stability is desired. Furthermore, various mechanisms such as spring-loaded or sliding mounts can be used to extend and/or retract the hooks 80.

The embodiments of the invention in which an exclusive property or privilege is claimed are defined as follows:

1. A portable defibrillator, comprising:
   a defibrillator circuit;
   a body for housing the defibrillator circuit; and
   a hook coupled to the body, wherein the hook is positionable in an extended position and a retracted position, and wherein the hook, when in the extended position, is poised to receive a member of an external structure, thereby enabling the defibrillator to hang from the external structure.

2. The portable defibrillator of claim 1, wherein the hook is positionable by rotating the hook between the extended and retracted positions.

3. The portable defibrillator of claim 1, wherein the hook is shaped to have an inner periphery complementing the exterior shape of the member of an external structure.

4. The portable defibrillator of claim 2, further comprising a slot defined in the body for coupling the hook to the body, the hook having a cylindrical pivot member transversely disposed to the curvature of the hook, such that when the cylindrical pivot member is received in the slot, the hook is coupled to the body and rotates between the extended and retracted positions.

5. The portable defibrillator of claim 4, wherein the body further includes a deflectable member positioned to engage a depression formed in the outer surface of the hook when the hook is in the extended position.

6. The portable defibrillator of claim 5, wherein the deflectable member has a protrusion defined thereon and the protrusion is positioned to engage the depression when the hook is in the extended position.

7. The portable defibrillator of claim 6, wherein the depression formed in the outer surface of the hook is a groove oriented parallel to the longitudinal axis of the cylindrical pivot member, and the protrusion defined on the deflectable member of the body is a lip that engages the groove when the hook is in the extended position.

8. The portable defibrillator of claim 7, wherein the outer surface of the hook further has an interior edge oriented parallel to and spaced apart from the groove, and where in the lip engages the interior edge when the hook is in the retracted position.

9. The portable defibrillator of claim 8, wherein the hook is a first hook and the portable defibrillator further comprises at least one other hook coupled to the body, the other hook rotatable between an extended position and a retracted position, wherein the other hook, in the extended position, is poised to receive a member of an external structure in cooperation with the first hook.

10. A portable defibrillator, comprising:

a defibrillator circuit;

a body for housing the defibrillator circuit, the body having a front and a base;

a hook coupled to the body, wherein the hook is positionable in an extended position and a retracted position, and wherein the hook, when in the extended position, is poised to receive a member of an external structure, thereby enabling the defibrillator to hang from the external structure; and a user interface panel disposed on the front of the body for providing information to and receiving information from a user of the defibrillator, the user interface panel oriented on the front of the body to face at an upward angle relative to the base.

11. The portable defibrillator of claim 10, wherein the defibrillator further comprises a monitor circuit for monitoring a physiological condition of a patient, and the user interface panel includes a display for displaying physiological data collected by the monitor circuit.

12. The portable defibrillator of claim 10, wherein the user interface panel is oriented on the front of the body to extend substantially above an obstruction when the defibrillator is placed behind the obstruction.

13. The portable defibrillator of claim 12, wherein the obstruction is a patient's legs and the defibrillator is placed between the legs of the patient lying in a horizontal position.

14. A portable defibrillator, comprising:

a defibrillator circuit;

a body for housing the defibrillator circuit, the body having a front and a base;

a hook coupled to the body for hanging the defibrillator from an external structure;

a user interface panel disposed on the front of the body for providing information to and receiving information from a user of the defibrillator, the user interface panel oriented on the front of the body to face at an upward angle relative to the base; and electrical connection sites for coupling external electronic instruments to the defibrillator, wherein the electrical connection sites are recessed back from the front of the defibrillator.

15. The portable defibrillator of claim 14, wherein the electrical connection sites are further disposed on a panel extending outward from a side of the defibrillator.

16. A portable defibrillator for use on a patient in a gurney, the gurney having a frame including a horizontally disposed bar, the portable defibrillator comprising:

defibrillator circuitry;

a body for housing the defibrillator circuitry, the body including a front, a rear, and a base, wherein progressing upward from the base of the body, the front of the body angles back toward the rear;

a hook connected to the body, wherein the hook is rotatable between an extended position and a retracted position, and wherein the hook, when in the extended position, may receive the horizontally disposed bar, and thereby permit the portable defibrillator to hang from the gurney; and a user interface disposed on the front of the body and oriented to face at an upward angle relative to the defibrillator base.

17. The portable defibrillator of claim 16, wherein the horizontally disposed bar is a first horizontal bar and the gurney frame further includes a second horizontal bar positioned below the first horizontal bar, and wherein when the defibrillator is hung by the hook from the first horizontal bar, the second horizontal bar contacts the rear of the body and thereby pushes the base of the body forward, rotating the body about an axis defined by the first horizontal bar.

18. A method of suspending a portable defibrillator from an external structure, comprising:

(a) coupling a hook to the portable defibrillator such that the hook is positionable in an extended position or a retracted position relative to the defibrillator;

(b) positioning the hook in the extended position;

(c) placing the defibrillator adjacent to the external structure, wherein the hook, in the extended position, receives a member of the external structure; and (d) releasing the defibrillator, thereby allowing the defibrillator to hang from the external structure via the defibrillator's extended hook.

19. The method of claim 18, wherein the step of positioning the hook comprises rotating the hook from the retracted position to the extended position.

20. The method of claim 18, wherein the external structure is a gurney having a frame and wherein the step of placing the defibrillator comprises lifting the defibrillator to a position adjacent the gurney frame and causing the extended hook to engage a member of the gurney frame.

21. A hook for use with a portable defibrillator that enables the portable defibrillator to hang from an external structure, the hook comprising:

a central body shaped with a generally bent configuration; and a cylindrical member connected to the central body, the cylindrical member extending transversely from the central body with respect to the curvature of the bent configuration of the central body, wherein the cylindrical member rotatably couples the hook to a portable defibrillator such that the hook is positionable in an extended or retracted position relative to the defibrillator.

22. The hook of claim 21, wherein the central body is sized to be received by a portable defibrillator when the hook is coupled to the portable defibrillator and is positioned in the retracted position.

* * * * *

UNITED STATES PATENT AND TRADEMARK OFFICE
CERTIFICATE OF CORRECTION

PATENT NO. : 5,935,152
DATED : August 10, 1999
INVENTOR(S) : R.J. Merry et al.

It is certified that error appears in the above-identified patent and that said Letters Patent is hereby corrected as shown below:

| COLUMN | LINE | |
|---|---|---|
| 8 | 63 | "where in" should read --wherein-- |
| (Claim 8, | line 3) | |

Signed and Sealed this

Seventeenth Day of October, 2000

Attest:

Q. TODD DICKINSON

Attesting Officer

Director of Patents and Trademarks